(12) United States Patent
Lee et al.

(10) Patent No.: US 8,119,977 B2
(45) Date of Patent: Feb. 21, 2012

(54) AERODYNAMIC LENS CAPABLE OF FOCUSING NANOPARTICLES IN A WIDE RANGE

(75) Inventors: Dong-Geun Lee, Pusan (KR); Kwang-Seung Lee, Jinhae-si (KR)

(73) Assignee: Pusan National University Industry-University Cooperation Foundation, Pusan (KR)

( * ) Notice: Subject to any disclaimer, the term of this patent is extended or adjusted under 35 U.S.C. 154(b) by 231 days.

(21) Appl. No.: 12/696,726

(22) Filed: Jan. 29, 2010

(65) Prior Publication Data

US 2011/0186167 A1 Aug. 4, 2011

(51) Int. Cl.
*H05H 3/00* (2006.01)
*H01J 49/26* (2006.01)

(52) U.S. Cl. ........ 250/251; 250/281; 250/282; 250/288; 250/287; 55/442; 55/445; 55/322; 95/267; 95/272

(58) Field of Classification Search ................... 250/251, 250/281, 282, 288, 287; 55/442, 445, 322; 95/267, 272
See application file for complete search history.

(56) References Cited

U.S. PATENT DOCUMENTS

| 5,565,677 | A * | 10/1996 | Wexler et al. | 250/251 |
| 6,924,004 | B2 * | 8/2005 | Rao et al. | 427/421.1 |
| 7,365,314 | B2 * | 4/2008 | Lee et al. | 250/287 |
| 7,652,247 | B2 * | 1/2010 | Lee et al. | 250/251 |

FOREIGN PATENT DOCUMENTS

KR 10-0744006 7/2007

OTHER PUBLICATIONS

English-language abstract of Publication N. 1020060102833.
John T. Jayne et al., "Development of an Aerosol Mass Spectrometer for Size and Composition Analysis of Submicron Particles," *Aerosol Science and Technology*, 33:1, pp. 49-70 (2000).
Xuefeng Zhang et al., "Numerical Characterization of Particle Beam Collimation: Part II Integrated Aerodynamic-Lens—Nozzle System," *Aerosol Science and Technology*, 38, pp. 619-638 (2004).
Xiaoliang Wang et al., "Aerodynamic Focusing of Nanoparticles: I. Guidelines for Designing Aerodynamic Lenses for Nanoparticles," *Aerosol Science and Technology*, 39, pp. 611-623 (2005).
Xiaoliang Wang et al., "An Experimental Study of Nanoparticle Focusing With Aerodynamic Lenses," *International Journal of Mass Spectrometry*, 258, pp. 30-36 (2006).
Sung-Lee Kwang et al., "Development and Experimental Evaluation of Aerodynamic Lens as an Aerosol Inlet of Single Particle Mass Spectrometry," *Journal of Aerosol Science* (2007).
Peter S. K. Liu et al., "Transmission Efficiency of an Aerodynamic Focusing Lens System: Comparison of Model Calculations and Laboratory Measurements for the Aerodyne Aerosol Mass Spectrometer," *Aerosol Science and Technology*, 41:8, pp. 721-733 (2007).

* cited by examiner

*Primary Examiner* — Nikita Wells
(74) *Attorney, Agent, or Firm* — Stein McEwen, LLP

(57) ABSTRACT

An aerodynamic lens includes a cylindrical hollow body having an inlet and an outlet, and first and second focusing parts formed in the body. The first focusing part includes a plurality of orifice lenses of which inner diameters (df) are gradually decreased in an advancing direction of particle. The second focusing part includes a plurality of orifice lenses of which inner diameters (df) are gradually increased in the advancing direction of particle.

6 Claims, 11 Drawing Sheets

AERODYNAMIC LENS CAPABLE OF FOCUSING NANOPARTICLES IN A WIDE RANGE

BACKGROUND OF THE INVENTION

1. Field of the Invention

The present invention relates to an aerodynamic lens, and more particularly to an aerodynamic lens capable of effectively focusing nanoparticles in a wide range, whose focusable size range is approximately two order of magnitude, e.g., 30~3,000 nm.

2. Description of the Related Art

As well known in the art, an aerodynamic lens focuses particles floating in the atmosphere to generate a particle beam. The aerodynamic lens is generally used together with a single particle mass spectrometer (SPMS) that analyzes chemical composition and size of a single particle in an aerosol state.

Such an aerodynamic lens is configured with multi-stage orifices and focuses particles by means of shrinkage/expansion of a carrier gas and inertia of the particles without any special mechanical or electric device. However, aerodynamic lenses suggested until now may focus particles whose particle sizes are just in the range of about 3~30 nm or 30~300 nm, where a maximum size is just about 10 times of a minimum size.

The range of focusable particle sizes is limited as above because too small particles are not easily focused and too great particles cause collision losses due to the inertia. Considering that the range of particle sizes allowing highly efficient focusing is limited as above, it is also impossible to efficiently focus particles with more variable sizes.

In addition, in case of an orifice nozzle provided at an outlet of a conventional aerodynamic lens, air is abruptly expanded at an outlet of the nozzle due to a great pressure difference between the front and rear portions of the nozzle throat, and after that, the velocity of the air is greatly decreased due to the compressibility effect. Such an air expansion/compressibility effect causes the air velocity to be relatively increased in a radial direction of the lens, thereby disturbing the focusing of a particle beam.

SUMMARY OF THE INVENTION

The present invention is designed to solve the problems of the prior art, and therefore it is an object of the present invention to provide an aerodynamic lens, which may focus particles so as to give excellent focusing ability and transmission efficiency with respect to particles whose sizes are distributed in a wider range where a maximum size is over 100 times of a minimum size, for examples particles with diameters in the range of 30~3,000 nm.

Another object of the present invention is to provide an aerodynamic lens having a convergence-divergence nozzle so as to prevent air from being abruptly expanded or compressed in an outlet nozzle.

To ensure efficient focusing in such a wide particle size range, there is needed a means for restraining inertia collision of particles with big diameter and preventing the focused particle beam from diverging again. Further, there is also needed a new-type nozzle design capable of easily accelerating particles with various sizes and preventing their divergence.

In order to accomplish the above object, the present invention provides an aerodynamic lens, which includes a cylindrical hollow body having an inlet and an outlet; and first and second focusing parts formed in the body, wherein the first focusing part includes a plurality of orifice lenses of which inner diameters (df) are gradually decreased in an advancing direction of particle, and wherein the second focusing part includes a plurality of orifice lenses of which inner diameters (df) are gradually increased in the advancing direction of particle.

Preferably, in the aerodynamic lens according to the present invention, Stokes numbers (St) of particles in the first focusing part may be gradually increased in the advancing direction of particle, and Stokes numbers (St) of particles in the second focusing part may be gradually decreased in the advancing direction of particle.

In detail, the first focusing part preferably includes first, second and third orifice lenses of which inner diameters are df1, df2 and df3, respectively, and the inner diameters may satisfy the following relation: df1>df2>df3.

In another embodiment, the second focusing part preferably includes fourth, fifth and sixth orifice lenses of which inner diameters are df4, df5 and df6, respectively, and the inner diameters may satisfy the following relation: df4<df5<df6.

In another aspect of the present invention, there is also provided an aerodynamic lens, which includes a cylindrical hollow body having an inlet and an outlet; a plurality of lenses formed in the body; and a convergence-divergence nozzle formed at an outlet of the body, wherein the convergence-divergence nozzle includes a nozzle hole formed at a center thereof to allow the passage of particle; and a convergence slant surface and a divergence slant surface formed at front and rear portions thereof to form a convergence angle ($\delta$) and a divergence angle ($\theta$) with respect to a central axis of the nozzle hole, respectively.

Preferably, the convergence angle ($\delta$) of the convergence-divergence nozzle is set greater than the divergence angle ($\theta$).

The aerodynamic lens according to the present invention may greatly increase a diameter range of focusable particles in comparison to the conventional cases by adopting first and second focusing parts whose particle focusing characteristics are distinguishable, and a convergence-divergence nozzle. In other words, the aerodynamic lens of the present invention may effectively focus particles with various sizes in the range of 30~3,000 nm while ensuring transmission efficiency of 90% or above and particle beam diameter less than 1 mm.

More detailed effects of the present invention will be more clearly understood through the following preferred embodiments.

BRIEF DESCRIPTION OF THE DRAWINGS

Other objects and aspects of the present invention will become apparent from the following description of embodiments with reference to the accompanying drawing in which.

DESCRIPTION OF THE PREFERRED EMBODIMENT

Hereinafter, preferred embodiments of the present invention will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

Figure 1:
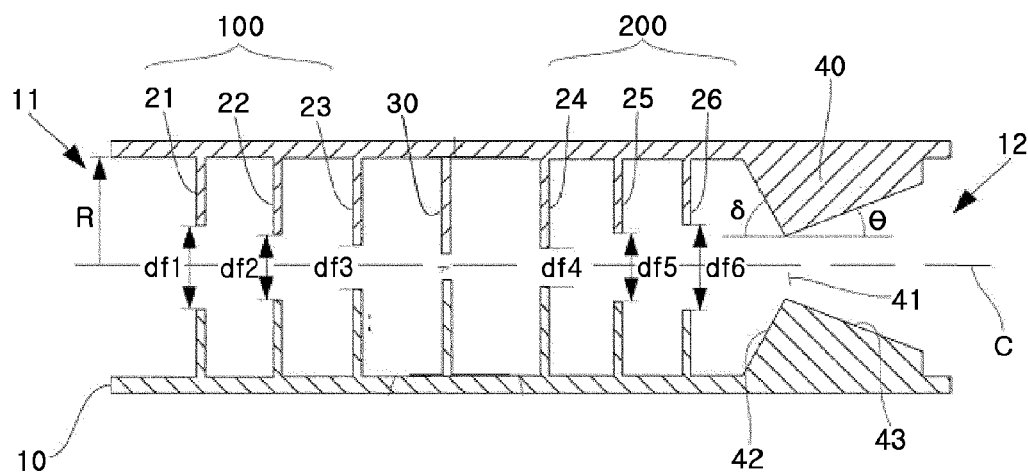
FIG. 1 is a schematic sectional view showing an aerodynamic lens according to a preferred embodiment of the present invention.

FIG. 1 is a schematic sectional view showing an aerodynamic lens according to a preferred embodiment of the present invention.

Referring to FIG. 1, the aerodynamic lens according to the present invention includes a cylindrical hollow body 10 having an inlet 11 and an outlet 12, a plurality of orifice lenses 21 to 26 formed in the body 10, and a convergence-divergence nozzle 40.

The inlet 11 may be exposed to the atmosphere in a region to be measured, and the outlet 12 may be connected to a chamber with a relatively low pressure such as a vacuum chamber of a single particle mass spectrometer (not shown).

Also, the convergence-divergence nozzle 40 is provided at the outlet 12 of the cylindrical body 10.

The aerodynamic lens of the present invention includes two focusing parts. A first focusing part 100 is used for focusing particles with relatively great diameters, for example about 300~3,000 nm, and the occurrence of inertia collision is controlled therein. Also, a second focusing part 200 is used for focusing particles with relatively small diameters and plays a role of controlling a particle beam already focused not to diverge again.

The first and second focusing parts 100, 200 are composed of a plurality of orifice lenses 21 to 23, 24 to 26, respectively. Preferably, the orifice lenses 21, 22, 23 of the first focusing part 100 have inner diameters df gradually decreasing in an advancing direction of particle. In other words, the diameter df1 of the first orifice lens 21 is greater than the diameter df2 of the second orifice lens 22, which is greater than the diameter df3 of the third orifice 23.

$$df1 > df2 > df3 \quad \text{Math Figure 1}$$

Figure 2:
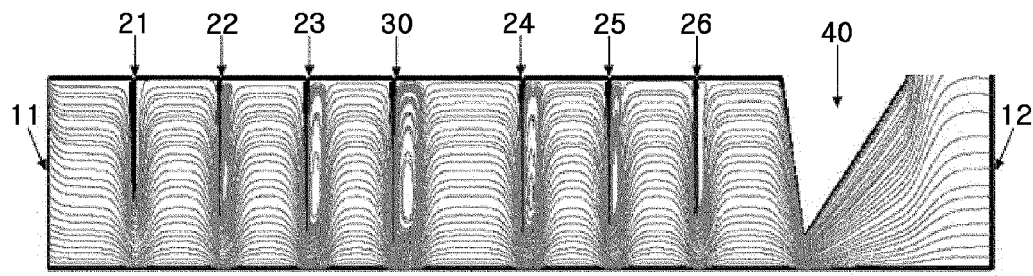
FIG. 2 is a diagram showing air flowing and boundary conditions in the aerodynamic lens according to the preferred embodiment of the present invention.

Meanwhile, the plurality of orifice lenses 24, 25, 26 of the second focusing part 200 are designed to have inner diameters df gradually increasing in the advancing direction of particle. In other words, the diameter df4 of the fourth orifice lens 24 is smaller than the diameter df5 of the fifth orifice lens 25, which is smaller than the diameter df6 of the sixth orifice lens 26.

$$df4 < df5 < df6 \quad \text{Math Figure 2}$$

Also, the convergence-divergence nozzle 40 is formed at the outlet of the cylindrical body 10. The convergence-divergence nozzle 40 has a nozzle hole 41 formed at a center thereof to allow the passage of particles. The convergence-divergence nozzle 40 also has a convergence slant surface 42 at the front of the nozzle hole 41 and a divergence slant surface 43 at the rear of the nozzle hole 41, respectively. At this time, the convergence slant surface 42 and the divergence slant surface 43 form a convergence angle $\delta$ and a divergence angle $\theta$ with respect to a central axis C of the aerodynamic lens, respectively. Preferably, the convergence angle $\delta$ is greater than the divergence angle $\theta$.

The diameters df of the orifice lenses may be suitably set depending on conditions. For example, it is known that, in case a ratio (df/OD) of the diameter df of the orifice lens to the outer diameter OD of the aerodynamic lens is 0.4 or more, the carrier gas does not easily converge or diverge, and thus particles are not optimally focused. Thus, in case the diameter df1 of the first orifice lens 21 is set as 8 mm, the outer diameter OD of the aerodynamic lens should be set as at least 20 mm, preferably about 25 mm.

Gaps among the lenses are preferably set not to cause a vortex among them.

Now, characteristics and effects of the aerodynamic lens according to the present invention, configured as above, are explained in more detail through specific experimental examples.

Conditions of Simulation

Numerical analysis program, FLUENT (Ver. 6.2.16), was used for simulating behavior and flowing of particles in the aerodynamic lens according to the present invention. Since the particles have low number-concentration and small sizes, interaction and effects among the particles were ignored.

A flow rate of introduced air at the inlet of the aerodynamic lens was limited to a general level (100 sccm, $2.042 \times 10^{-6}$ kg/s) of an aerosol mass spectrometer. Also, a pressure at the outlet of the aerodynamic lens was assumed as a constant value, $10^{-3}$ torr (~0.13 pa), that is a pressure condition of a mass analyzer. In addition, a calculation region was reduced based on the axis-symmetric property. The carrier gas was assumed to have compressive laminar viscous flowing of a normal state, and particles were assumed as standard spherical particles with a density of ~1 g/cc. Brownian motion was ignored with respect to particles of 30 nm or more. Also, the whole gas flow was considered as continuum. In addition, all results mentioned herein were obtained based on Near-axis conditions unless any special mention is made.

Figure 3:
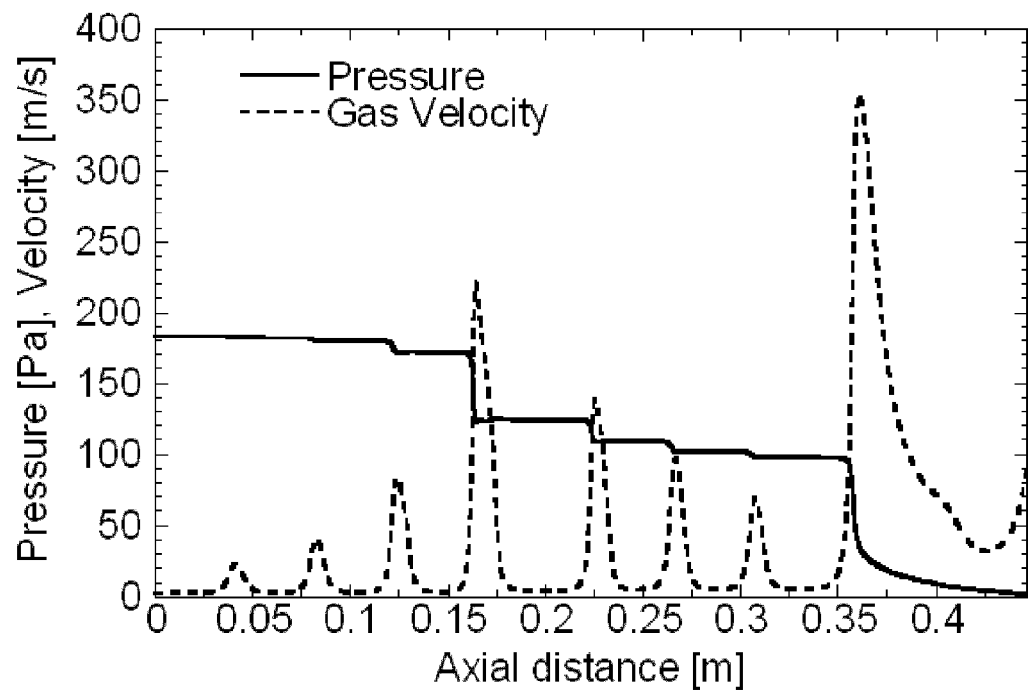
FIG. 3 is a graph showing a pressure field and a velocity field of the air serving as a carrier gas in or out of the aerodynamic lens according to the preferred embodiment of the present invention.

The behavior of particles at the front and rear portions of the orifice lens are represented by Stokes number St and defined in accordance with the following math FIG. 3 {Aerodynamic Focusing of Nanoparticles: I. Guidelines for Designing Aerodynamic Lenses for Nanoparticles; Xiaoliang Wang, Frank Einar Kruis, and Peter H. McMurry; Aerosol Science and Technology, 39: 611-623, 2005, and Development and experimental evaluation of aerodynamic lens as an aerosol inlet of single particle mass spectrometry; Kwang-Sung Lee, Sung-Woo Cho, Donggeun Lee; Journal of Aerosol Science, 39; 287-304, 2008}. The same definition as above is also applied to the convergence-divergence nozzle.

$$St = \frac{1}{\left(1 + \frac{\pi\varepsilon}{8}\right)\sqrt{2\pi\gamma^3}} \frac{\dot{m}\rho_p d_p c^3}{p_{ud}^2 d_i^3}$$ Math Figure 3

Streamline of Air and Stokes Number

FIG. 2 shows air flows in the aerodynamic lens according to the present invention and trajectories of the air in consideration of boundary conditions. Also, the following table 1 shows the change of Stokes number St in accordance with the diameter D of particles passing through the aerodynamic lens.

TABLE 1

| | Lens number | | | | | | |
|---|---|---|---|---|---|---|---|
| | 1 | 2 | 3 | 4 | 5 | 6 | 7 |
| St of 30 nm particles | 0.02 | 0.04 | 0.11 | 0.38 | 0.26 | 0.17 | 0.12 |
| St of 100 nm particles | 0.06 | 0.13 | 0.36 | 1.27 | 0.86 | 0.57 | 0.38 |
| St of 500 nm particles | 0.30 | 0.65 | 1.81 | 6.35 | 4.29 | 2.87 | 1.92 |
| St of 1 µm particles | 0.60 | 1.29 | 3.63 | 12.71 | 8.59 | 5.74 | 3.86 |
| St of 3 µm particles | 1.80 | 3.88 | 10.88 | 38.12 | 25.77 | 17.23 | 11.51 |
| Upstream Pressure [Pa] | 182.6 | 181.5 | 179.5 | 171.0 | 124.0 | 108.5 | 101.0 |
| Re | 16.0 | 20.5 | 28.8 | 42.3 | 30.0 | 24.0 | 20.0 |

Referring to FIG. 2 and Table 1, it would be understood the Stokes number St is increased from the first orifice lens to a center lens 30 with respect to all particles, and the Stokes number St is gradually decreased after that. For example, in case of a particle with a diameter D of 1,000 nm (D=1,000 nm), the Stokes number St at the first orifice lens 21 is 0.6, but the Stoke number St is rapidly increased to 12.71 at the center lens 30, and then the Stokes number St is greatly decreased at the sixth orifice lens 26.

An optimal focusing particle diameter Do at the first orifice lens 21 is 2,000 nm. In case a particle with a diameter D of 3,000 nm (D=3,000 nm) enters, the Stoke number St is about 1.8. As in this case, if the particle of D=3,000 nm has a low Stokes number, inertia collision at the first orifice lens 21 may be prevented to the maximum. It is very important since inertia collision of particles in the aerodynamic lens mostly occurs at the first orifice lens 21.

In addition, optimal focusing particle diameters Do from the second to sixth orifice lenses 22 to 26 are 100 nm to 500 nm, so it would be understood that particles in the range are optimally focused.

Pressure and Velocity of Carrier Gas

FIG. 3 shows a pressure field and a velocity field of the air serving as a carrier gas in or out of the aerodynamic lens according to the present invention. Pressure is relatively high in the first focusing part 100 and relatively low in the second focusing part 200.

Also, the velocity field is gradually increased in the first focusing part 100 but gradually decreased in the second focusing part 200.

Degree of Focusing with Respect to Each Particle

Figure 4:
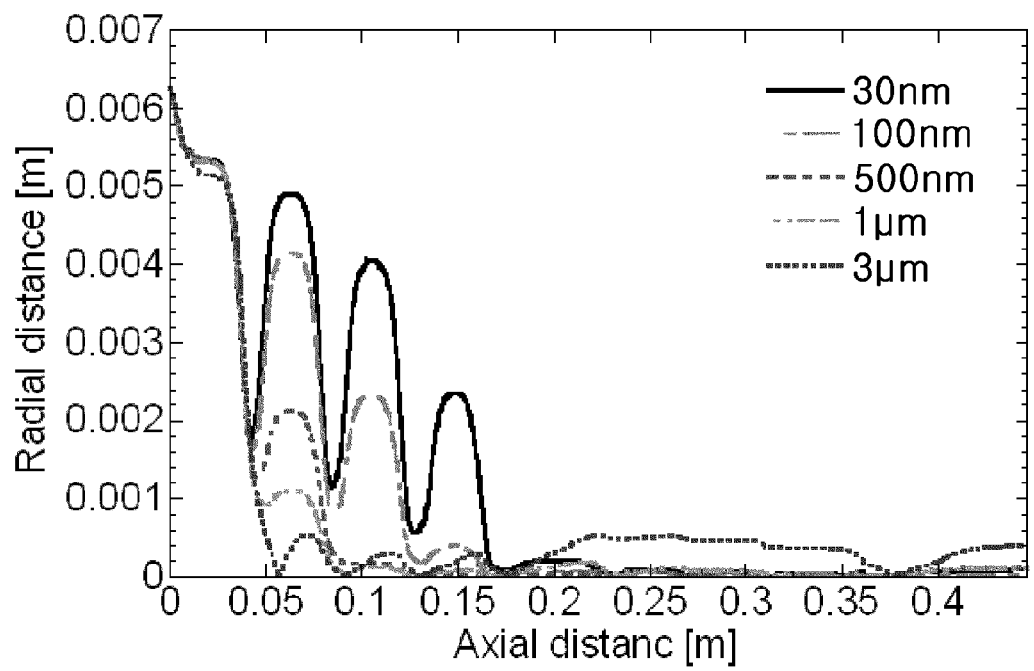
FIG. 4 is a graph showing the degree of focusing with respect to each particle size when an initial radial particle entrance location $r_i$ is 6.5 mm ($r_i$=6.5 mm) in the aerodynamic lens according to the preferred embodiment of the present invention.

FIG. 4 is a graph showing the degree of focusing with respect to each particle size when an initial radial particle entrance location $r_i$ is 6.5 mm ($r_i$=6.5 mm) in the aerodynamic lens according to the preferred embodiment of the present invention.

As shown in FIG. 4, it would be understood that the particles having a diameter D of 30 nm (D=30 nm) are substantially not focused due to a seriously low Stokes number St but focused after passing through the center lens 30.

On the contrary, in the case of particles of D=1,000 nm, the particles are focused at the first focusing part 100 to the maximum, and a radius of a particle beam becomes 0.25 mm. Also, while passing through the center lens 30, the particles diverge due to over-focusing since they pass through a region with a great Stokes number. However, the particle beam diverging in this case has a smaller diameter than in the case of particles with a diameter of 30 nm, because the diameter is affected by radial locations of the particles before passing through the center lens 30. Thus, though the particles have an increased diameter and pass through a lens with a great Stoke number St, the divergence of the beam may be controlled if a radial entrance location $r_o$ is sufficiently small before the particles enter the lens. Moreover, it is also possible to reduce inertia collision occurring at the front wall of the orifice.

In addition, in case of particles with diameters D of 1,000 nm and 3,000 nm (D=1,000 nm and D=3,000 nm), it would be found that, after the particles passes through the center lens 30 and diverge, the particles slightly diverge or progress in parallel while substantially not diverging. It is because the Stokes number St is rapidly decreased in the advancing direction of particle.

Behavior in First Focusing Part

Figure 5:
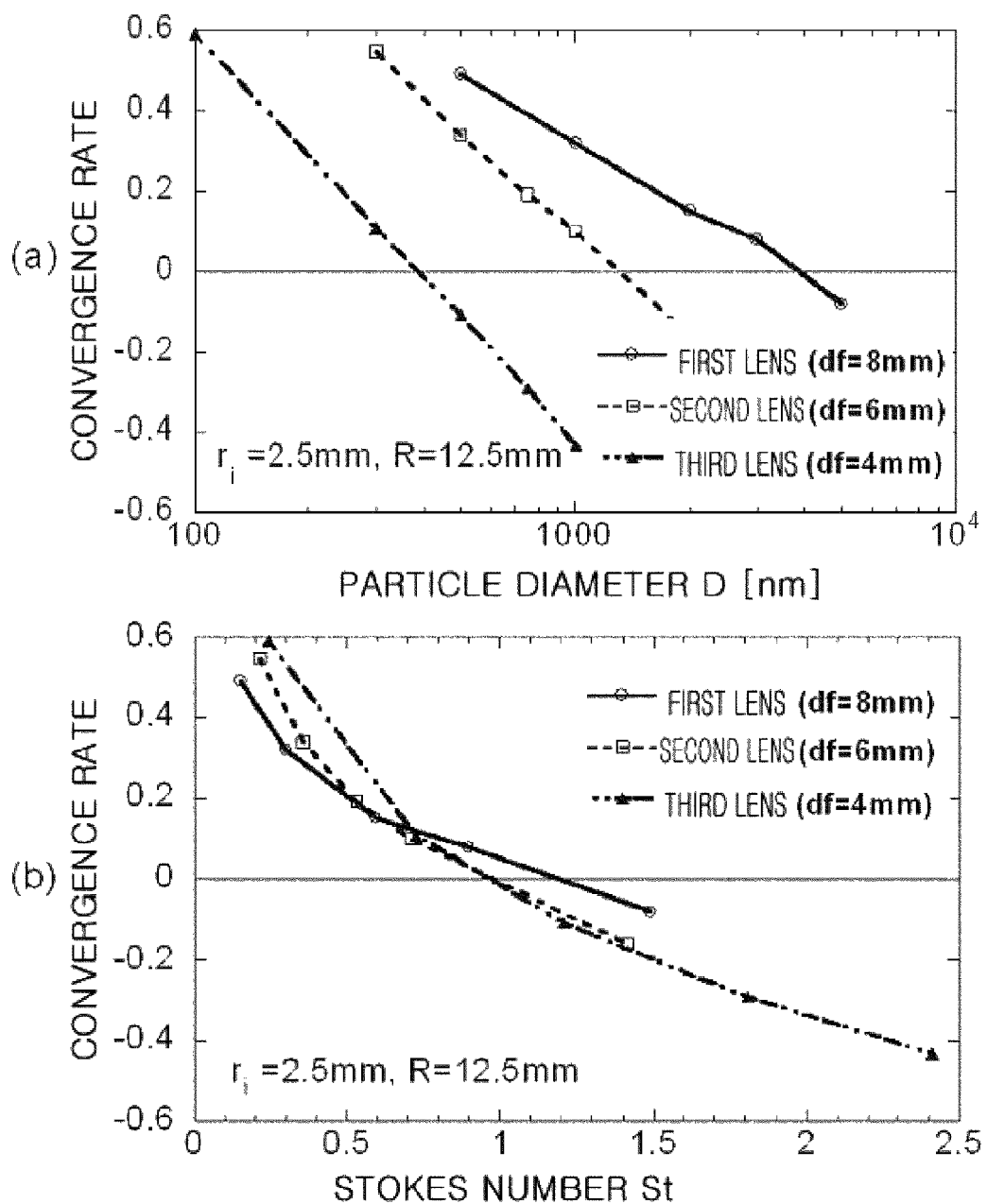
FIG. 5 is a graph showing the degree of focusing in accordance with particle size and Stokes number (St) in a first focusing part of the aerodynamic lens according to the preferred embodiment of the present invention.

FIG. 5 shows the degree of focusing in accordance with particle size and Stokes number (St) in the first focusing part 100. In this embodiment, the radius R of the aerodynamic lens is 12.5 mm, and an initial particle entrance location $r_i$ in a radial direction is 2.5 mm. Thus, $r_i/R=0.2$ is selected for the Near-Axis condition.

The optimal focusing particle diameter Do of the first orifice lens 21 is 4,000 nm, which has a low Stokes number St for particles of D=1,000 nm or above. Also, a divergence rate is within 0.5 with respect to particles of D=500~5,000 nm. Thus, after the particles of such sizes pass through the orifice lens, the radial location may be reduced below a half in comparison to the initial entrance location.

Figure 6:
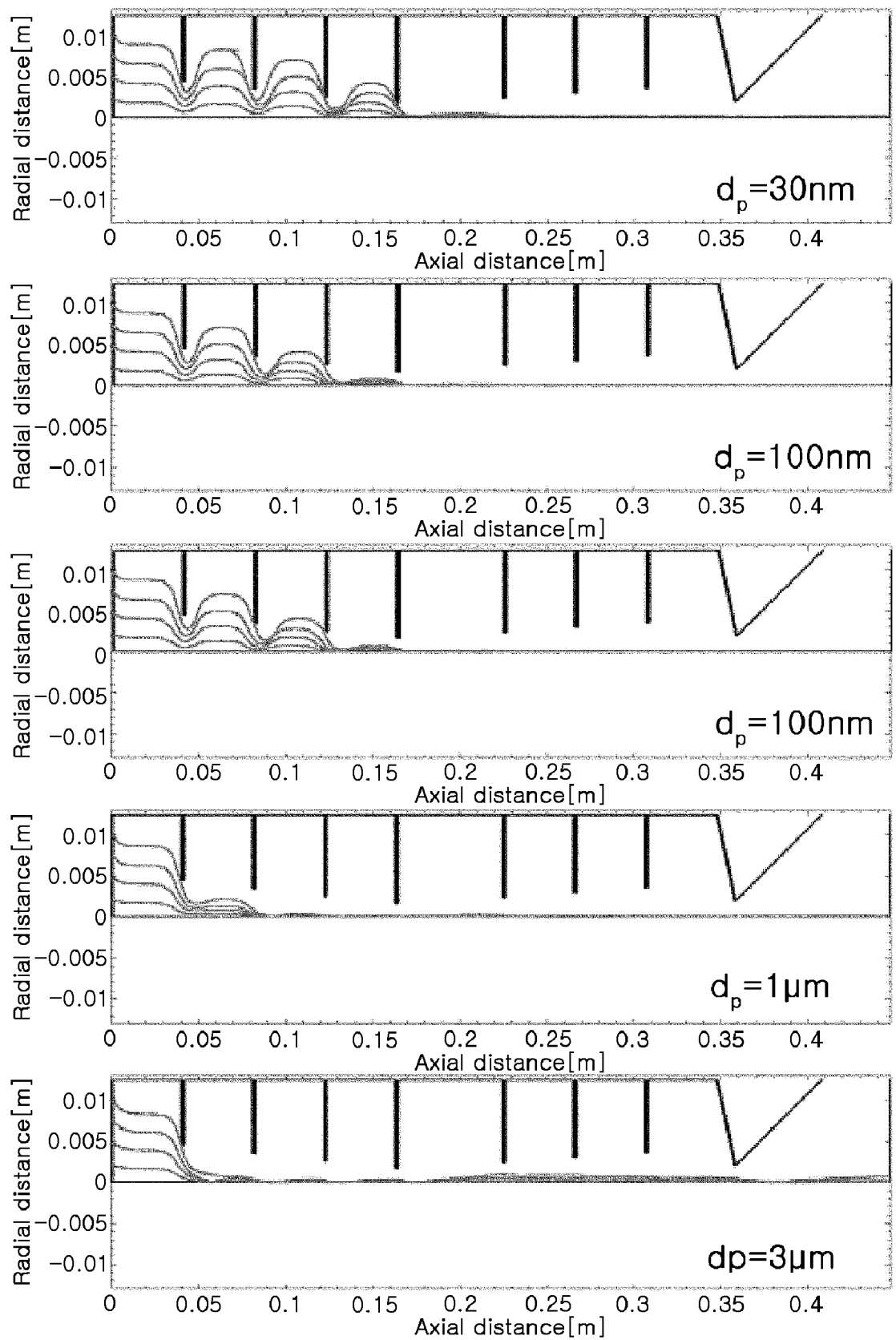
FIG. 6 shows simulation results of particle trajectories in the first focusing part and the second focusing part of the aerodynamic lens according to the preferred embodiment of the present invention.

FIG. 6 shows an actual simulation result of particle trajectories in the first focusing part 100 and the second focusing part 200.

Particles of D=100 nm or less have a particle beam radius of 1.2 mm at the end of the first focusing part 100, which gives somewhat insufficient focusing. However, particles of D=300~3,000 nm have a very regular particle beam radius of 0.23~0.25 mm and exhibit generally excellent focusing performance.

Meanwhile, particles of D=3,000 nm are sufficiently focused in the first focusing part 100. However, as the particles pass through the second focusing part 200, the particle beam focused in the first focusing part 100 restrains divergence at the second focusing part 200 since the Stokes numbers St at the center lens 30 and the fourth orifice lens 24 are respectively 38.12 and 25.77, which are significantly high. Thus, while keeping focused to some extent, these particles are preferably focused at the convergence-divergence nozzle 40. As a result, it would be understood that the first focusing part 100 focuses particles of D=300~1,000 nm into a particle beam with a radius less than 0.25 mm.

Figure 7:
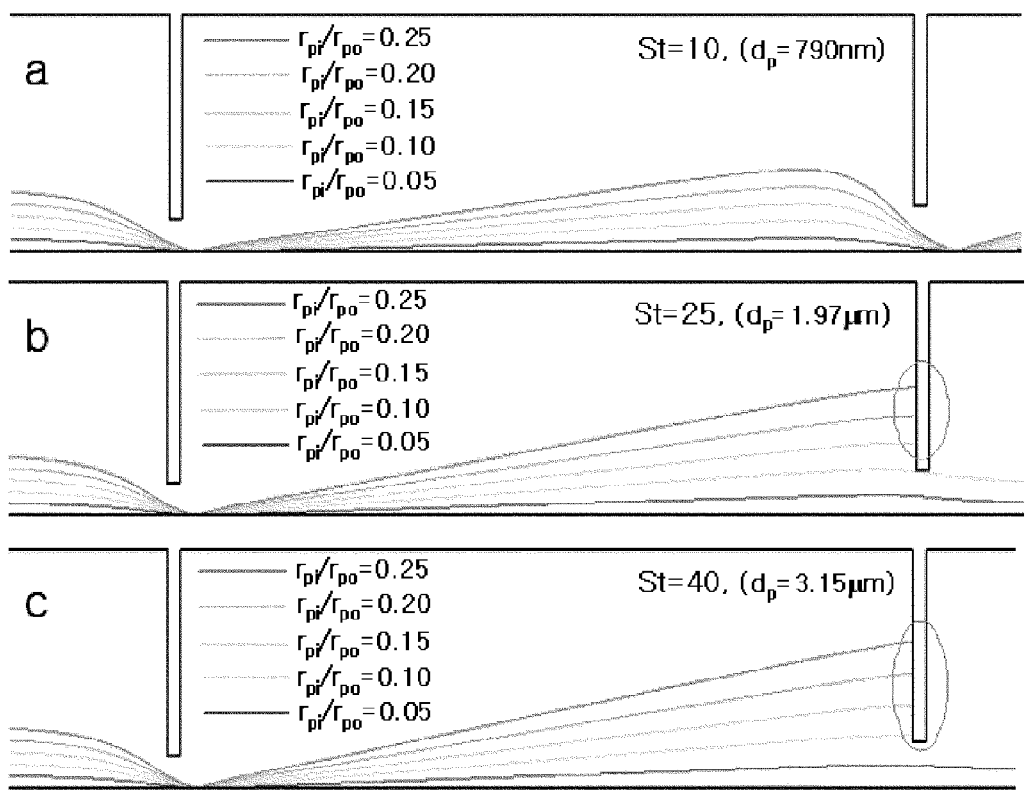
FIG. 7 is a graph showing the degree of inertia collision at an orifice wall in accordance with an initial entrance location ($r_i$) of particle at a center lens of the aerodynamic lens according to the preferred embodiment of the present invention.

FIG. 7 shows the degree of inertia collision at an orifice wall in accordance with an initial entrance location ($r_i$) of particle at the center lens 30. This region has a Stokes number St of 10 or above when particles of D=800 nm or more enters, so it has been revealed that inertial collision may occur in the region.

However, though particles have a diameter of D=3,000 nm and the Stokes number St exceeds 30, it could be understood that an inertia collision rate is changed depending on a radial entrance location of particle, so the loss caused by collision is zero if $r_i=1$ mm. Thus, a loss rate caused by the inertial collision of particle is changed in accordance with the Stokes number St but also dependent on a radial entrance location of particle.

In case a radial initial entrance location $r_i$ is less than 1 mm as shown in FIG. 7, a collision loss never occurs regardless of the particle size. However, it could be found that the collision loss is increased as the radial initial entrance location $r_i$ increases over 2 mm. In addition, in case the Stokes number St is low to have a particle size D less than 800 nm, particles pass without loss regardless of their entrance locations.

Seeing the collision loss in accordance with the Stokes number St as in FIG. 7, it could be understood that a particle loss abruptly occurs when the Stokes number St is more or less 10. As a result, a collision caused by inertia does not occur regardless of the particle size if the radial initial entrance location $r_i$ is less than 1 mm, and also a loss does not occur when the particle size is small.

Thus, if the particles of D=300~3,000 nm is changed into a particle beam with a radius less than 1 mm in the first focusing part 100, the collision loss caused by inertia does not occur in the entire aerodynamic lens. Since particles with such a great diameter are firstly focused at the orifice lenses of the first focusing part 100 with low Stokes numbers St, it is possible to prevent any particle collision loss even in the second focusing part 200.

Behavior in Second Focusing Part

Figure 8:
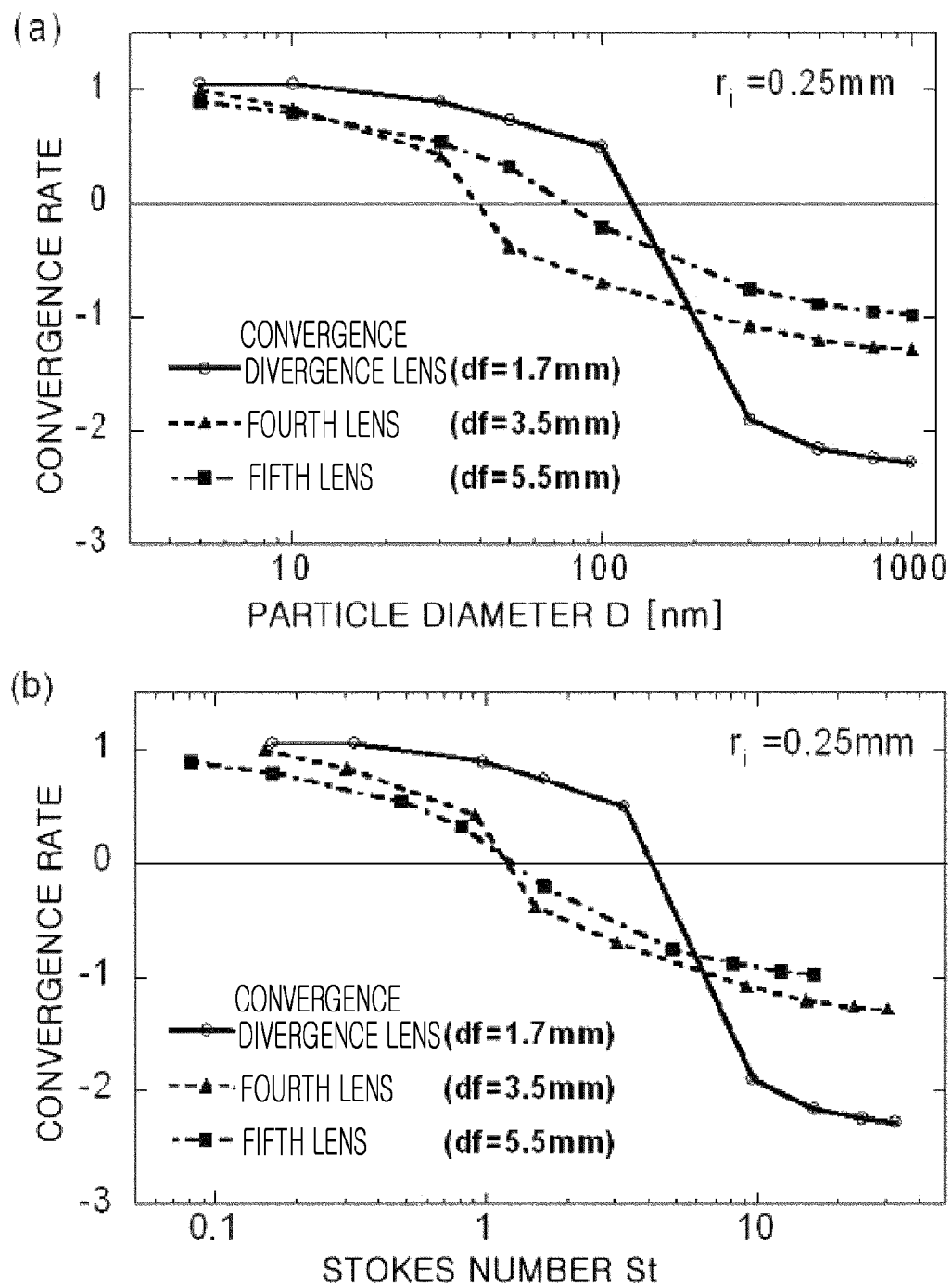
FIG. 8 is a graph showing the degree of focusing of particles in accordance with particle size and Stokes number (St) in the second focusing part of the aerodynamic lens according to the preferred embodiment of the present invention.
Figure 9:
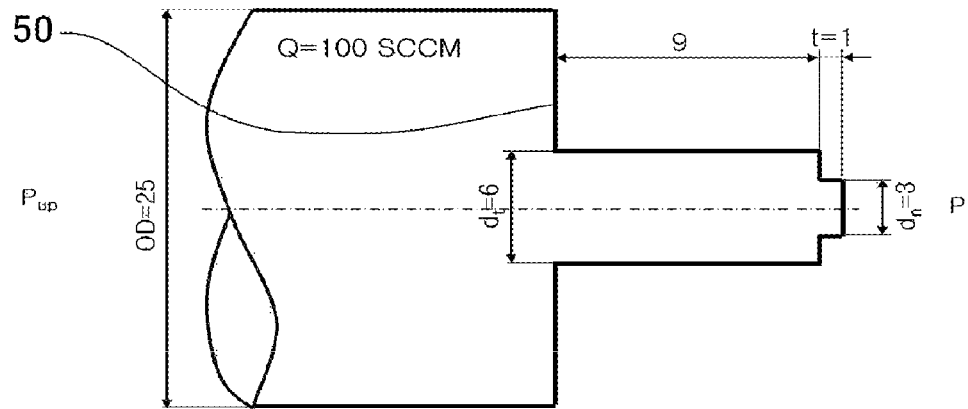
FIG. 9 is a schematic view showing a convergence-divergence nozzle employed in the aerodynamic lens according to the preferred embodiment of the present invention in comparison with a conventional orifice nozzle.
Figure 9:
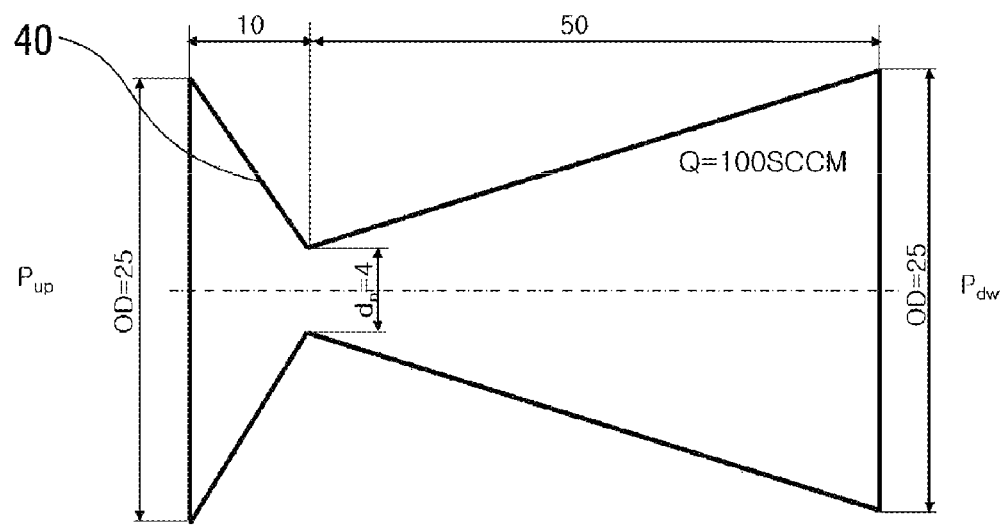
Figure 10:
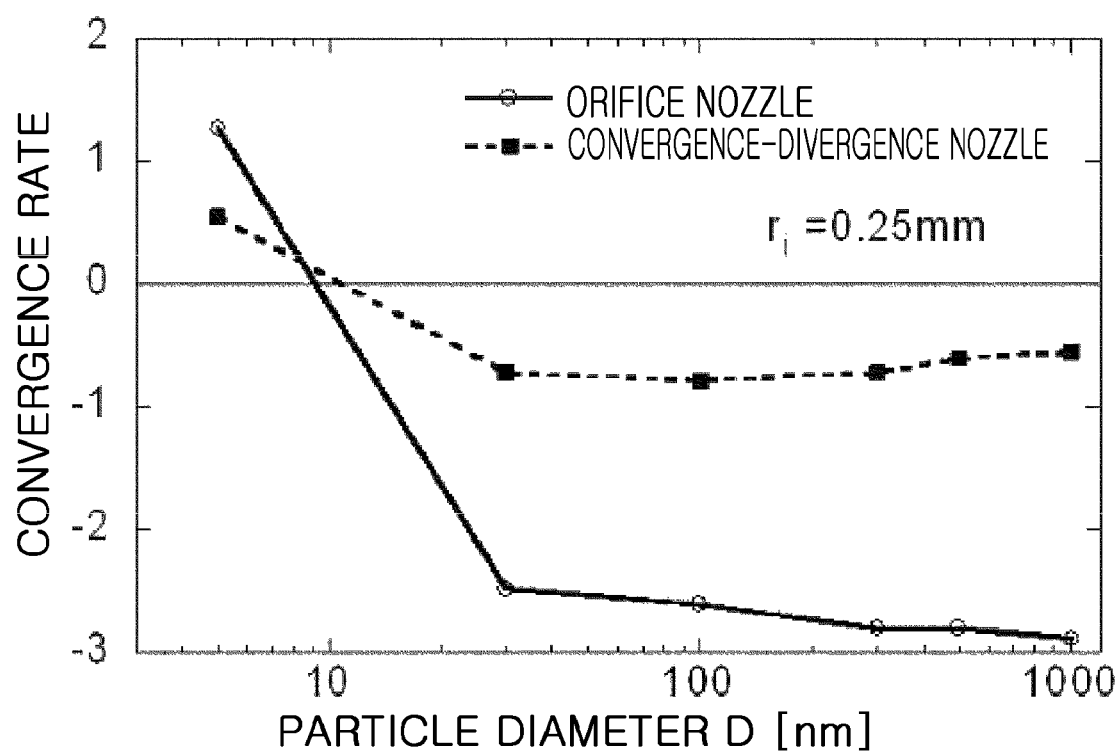
FIG. 10 is a graph showing focusing characteristics at the orifice nozzle and the convergence-divergence nozzle shown in FIG. 9.

FIG. 8 shows a numerical analysis result for a particle convergence rate in the second focusing part 200 under the condition of $r_i=0.25$ mm. In case particles have a specific particle size, if the particles are optimally focused by a lens, the particles are focused to have a particle beam radius of approximately 0.1~0.001 mm, which is very excellent. Thus, it may be considered that the particle beam substantially agrees with an axis.

However, particles of other sizes are not optimally focused, and a particle beam radius is approximately 0.1~0.5 mm, which is somewhat great. Most particles pertain to this region. The radius value, r=0.25 mm, means an average of particle beam radii obtained by focusing most particles. Also, what is concerned is how a convergence rate is changed when the beam already focused in the first focusing part 100 or the second focusing part 200 passes each lens.

Seeing the convergence rate result in accordance with Stokes number St in FIG. 8*b*, the convergence rate approaches 1 when particles pass through a region with a small Stokes number St. Thus, it could be understood that, in case a particle beam with a radius of 0.25 mm passes through a lens, if the Stokes number St is too small, the particle beam keeps its original shape without any convergence or divergence, and thus the radial particle location r after passing through the lens is 0.25 mm.

On the contrary, in case the Stokes number St is greatly increased over 6, particles are over-focused to have a convergence rate of −1 or less. Thus, the divergence is increased rather than the case of the initial entrance location, and the radial particle location r becomes over 0.25 mm.

Convergence-Divergence Nozzle

FIG. 9 shows specifications of the convergence-divergence nozzle 40 according to the preferred embodiment of the present invention and a conventional orifice nozzle selected as a comparative example. The convergence-divergence nozzle has a throat diameter dn of 4 mm (dn=4 mm), and the orifice nozzle has a throat diameter dt of 6 mm (dt=6 mm). Also, pressures $P_{up}$ at the upper ends of the nozzles are set to 92 Pa and 152 Pa, respectively. The entire nozzle lengths are respectively 60 mm and 10 mm, so the convergence-divergence nozzle 40 is longer than the conventional orifice nozzle 50.

Focusing characteristics at the orifice nozzle and the convergence-divergence nozzle are comparatively shown in FIG. 10. Referring to FIG. 10, it could be understood that the convergence-divergence nozzle of the present invention exhibits very excellent focusing characteristics in comparison to the conventional orifice nozzle. In particular, since the convergence-divergence nozzle of the present invention exhibits a convergence rate of more or less 0.5 regardless of particle size, it would be understood that the particle beam diameter is less than a half of the entrance radius.

FIG. 11 shows simulation results of air velocity distribution, which is one of air flowing characteristics at the front and rear portions of the orifice nozzle and the convergence-divergence nozzle. FIG. 11*a* depicts air velocity distribution at the nozzle in an axial direction. In the orifice nozzle, the axial velocity distribution is narrow and sharp since the air is abruptly expanded and then compressed after the nozzle throat. Meanwhile, in the convergence-divergence nozzle, the velocity reaches its peak as particles pass through the nozzle throat, and then the velocity is gradually decreased.

FIG. 11*b* depicts air velocity distribution at the nozzle in a radial direction. The radial velocity distribution is remarkably distinguishable at the comparison between air velocity distributions of the orifice nozzle and the convergence-divergence nozzle. A negative value at the radial velocity means that particles move toward the central axis and thus converge. On the contrary, a positive value means that particles diverge. Both axial and radial air velocity distributions give an influence on divergence and focusing of particle beam at the nozzle.

Figure 11:
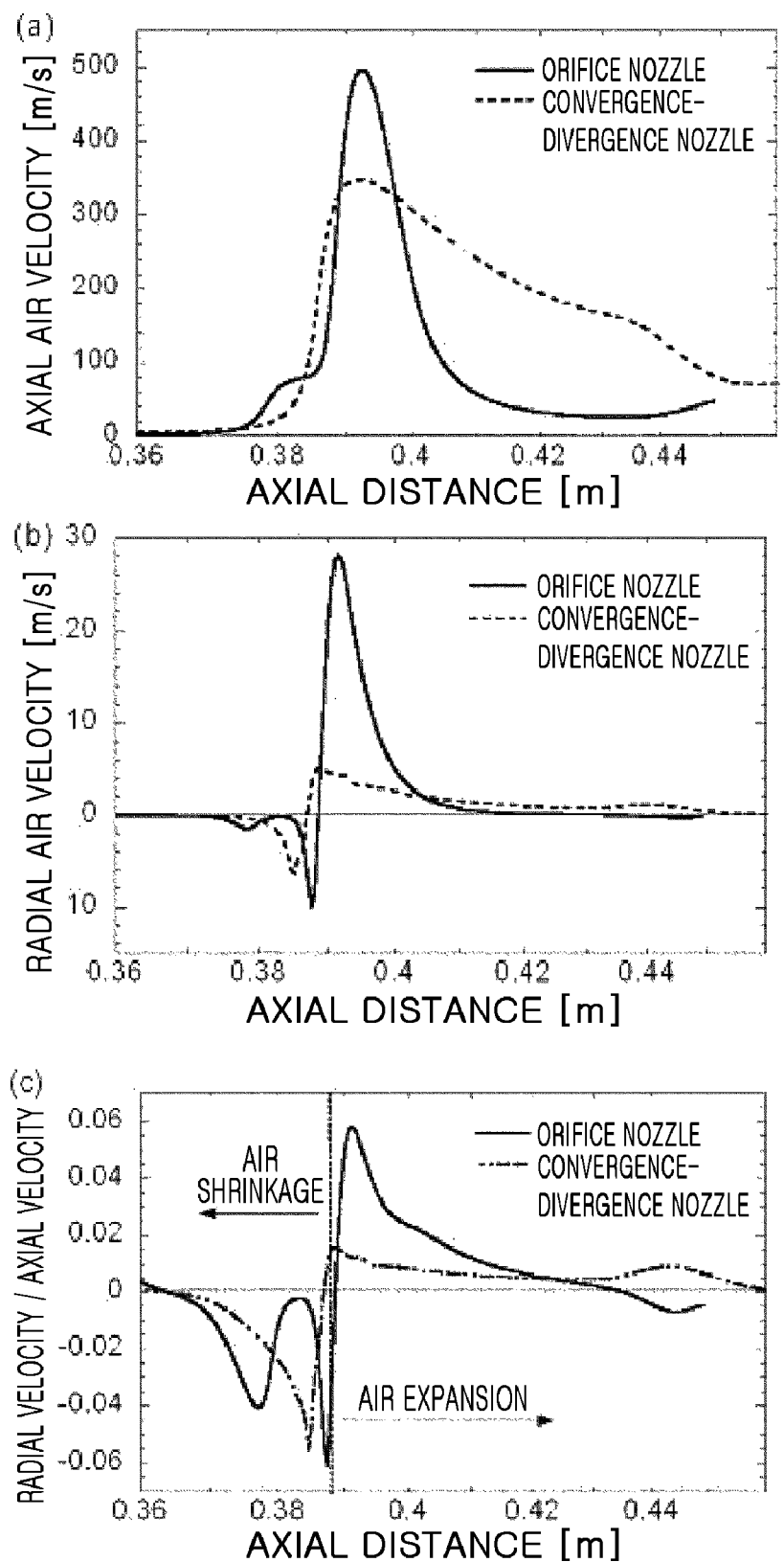
FIG. 11 is a graph showing simulation results of air velocity distribution at the convergence-divergence nozzle employed in the preferred embodiment of the present invention and the conventional orifice nozzle.

FIG. 11c depicts a ratio of radial velocity distribution to axial velocity distribution at the orifice nozzle and the convergence-divergence nozzle. Before air passes through the throat of the nozzle, ratios of radial velocity to an axial velocity with respect to a convergence direction at both nozzles are similar to each other. However, the ratios are remarkably different from each other at a portion after the nozzle throat where air is expanded. As a result, it could be understood that the convergence-divergence nozzle exhibits a similar velocity for a shrinking air but a relatively greatly low velocity for an expanding air in comparison to the orifice nozzle. In addition, the decrease of air expanding velocity becomes a factor that decreases the degree of divergence of particles.

Figure 12:
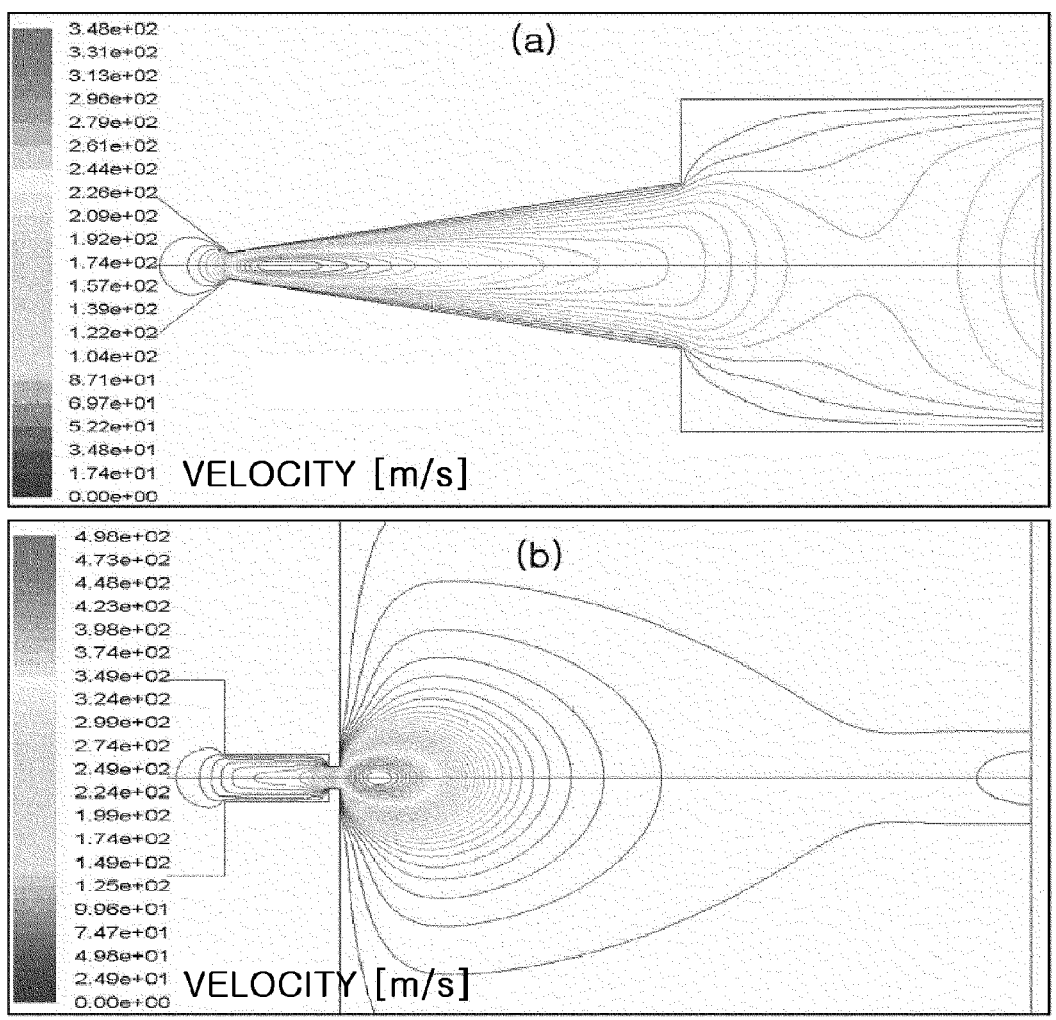
FIG. 12 is a schematic view showing the distributions of air velocity fields at the convergence-divergence nozzle employed in the preferred embodiment of the present invention and the conventional orifice nozzle.

FIG. 12 is a schematic diagram showing distribution of an air velocity field at the convergence-divergence nozzle and the orifice nozzle. At the convergence-divergence nozzle shown in FIG. 12a, ultrasonic wave is generated just after the nozzle throat, so the air velocity is gradually decreased. However, since iso-velocity lines run as a long oval shape, the velocity is smoothly decreased in comparison to the case of the orifice nozzle shown in FIG. 12b. Also, the geometric shape of the nozzle divergence portion controls a radial velocity below a suitable level.

At the orifice nozzle of FIG. 12b, air is abruptly expanded at the nozzle outlet due to the great difference of pressures before and after the nozzles. After that, the velocity is greatly decreased due to the compressibility effect. Since the air is expanded and then compressed, the radial air velocity is relatively increased. As a result, such an air flowing at the nozzle outlet is similar to that shown in FIG. 11, which is a proof that the convergence-divergence nozzle is more advantageous in focusing particles.

Evaluation of Performance of Aerodynamic Lens

Figure 13:
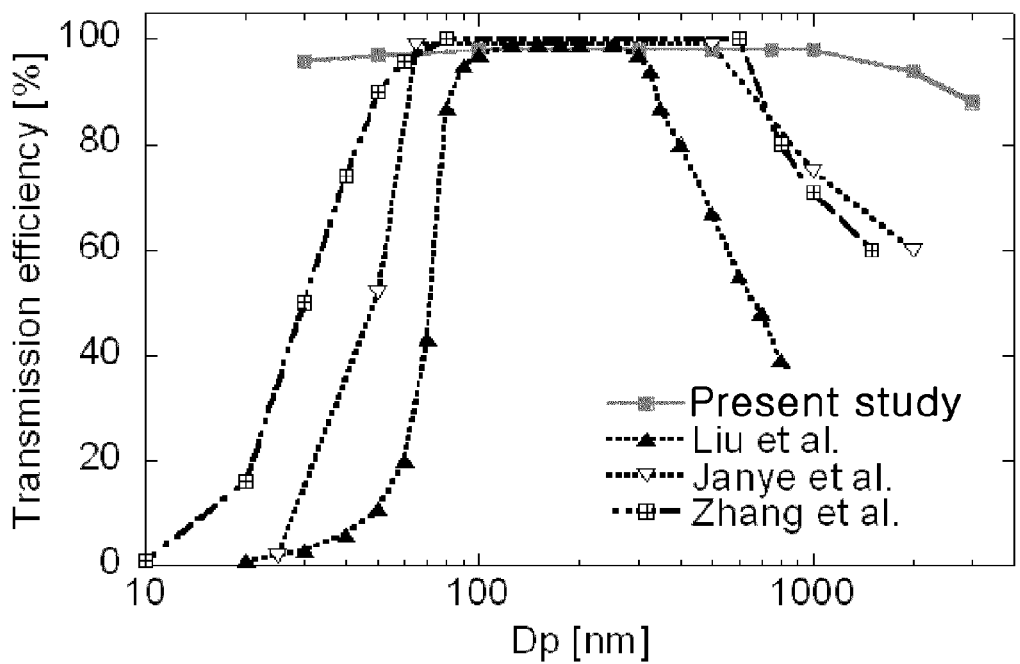
FIG. 13 is a graph showing particle transmission efficiencies with respect to particles with sizes of 30~3,000 nm in the aerodynamic lens according to the preferred embodiment of the present invention.

FIG. 13a shows particle transmission efficiency of the aerodynamic lens according to the present invention in comparison to numerical analysis results of conventional studies.

The conventional studies depicted as comparative examples are respectively simulations in accordance with Liu et al. (Transmission Efficiency of an Aerodynamic Focusing Lens System: Comparison of Model Calculation and Laboratory Measurements for the Aerodyne Aerosol Mass Spectrometer; Peter S. K. Liu et al.; Aerosol Science and Technology, 41:721-733, 2007), Wang el al. (An Experimental Study of Nanoparticle Focusing with Aerodynamic Lenses; Xiaoliang Wang, and Peter H. McMurry; International Journal of Mass Spectrometry, 258:30-36, 2006), Jayne et al. (Development of an Aerosol Mass Spectrometer for Size and Composition Analysis of Submicron Particle; John T. Jayne et al.; Aerosol Science and Technology, 33:49-70, 2000), and Zhang et al. (Numerical Characterization of Particle Beam Collimation: Part II Integrated Aerodynamic-Lens-Nozzle System; Xuefeng Zhang et al.; Aerosol Science and Technology, 38:619-638, 2004).

The aerodynamic lens of the present invention gives excellent transmission efficiency performance of 90% or above over a wide particle diameter range of D=30~3,000 nm.

The simulation results of Jane et al., Zhang et al. and Liu et al. represent transmission efficiencies with respect to particles with diameter of 10~1,000 nm, all of which exhibit greatly low transmission rates at 50 nm or less and tend to show decreased transmission efficiency due to the inertia collision loss at the lens.

As a result, it could be understood that the aerodynamic lens according to the present invention shows high transmission efficiency characteristics since it sufficiently focuses small particles of 100 nm or less and remove inertia collision at the lens with respect to large particles of 300 nm or more.

Figure 14:
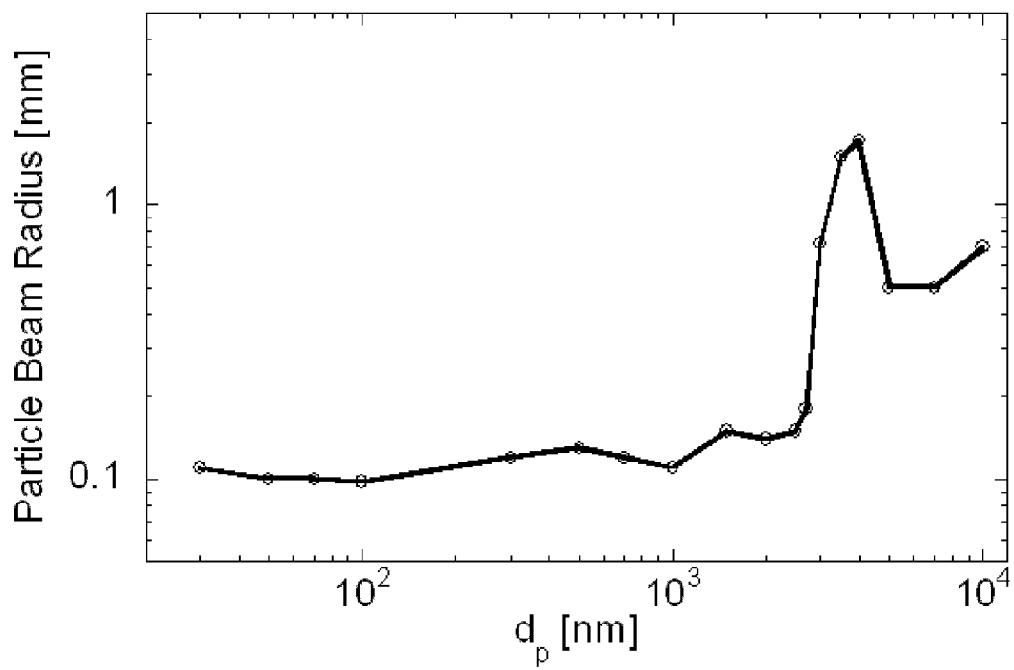
FIG. 14 is a graph showing results of numerical analysis for a diameter of particle beam focused by the aerodynamic lens according to the present invention.

FIG. 14 shows results of numerical analysis for a diameter of particle beam focused by the aerodynamic lens according to the present invention. As disclosed by Lee et al. (Development and experimental evaluation of aerodynamic lens as an aerosol inlet of single particle mass spectrometry; Kwang-Sung Lee, Sung-Woo Cho, Donggeun Lee; Journal of Aerosol Science, 39; 287-304, 2008), the result is a beam diameter measured at a location spaced from the nozzle end by 40 mm.

Such focusing characteristics of the present invention are obtained from the air flowing characteristics of the convergence-divergence nozzle and due to the fact that the inertia of particle is decreased and thus the influence of flowing becomes greater as a particle size is smaller. Compared with the particle beam diameter simulation of Lee et al. with respect to particles with diameter of D=30~300 nm, the focusing ability is similar with respect to particles with diameter of D=50~300 nm, so there is no serious difference. In view of the overall particle focusing ability, it could be understood from the simulation that particles with diameter of D=30~3,000 nm are changed into a particle beam with a diameter less than 1 mm, and particles with diameter D greater than 3,000 nm are changed into a particle beam with a diameter less than 2 mm.

What is claimed is:

1. An aerodynamic lens, comprising:
a cylindrical hollow body having an inlet and an outlet; and
first and second focusing parts formed in the body,
wherein the first focusing part includes a plurality of orifice lenses of which inner diameters (df) are gradually decreased in an advancing direction of particle, and
wherein the second focusing part includes a plurality of orifice lenses of which inner diameters (df) are gradually increased in the advancing direction of particle.

2. The aerodynamic lens according to claim 1,
wherein Stokes numbers (St) of particles in the first focusing part are gradually increased in the advancing direction of particle, and
wherein Stokes numbers (St) of particles in the second focusing part are gradually decreased in the advancing direction of particle.

3. The aerodynamic lens according to claim 1,
wherein the first focusing part includes first, second and third orifice lenses of which inner diameters are df1, df2 and df3, respectively, and
wherein the inner diameters satisfy the following relation:

df1>df2>df3.

4. The aerodynamic lens according to claim 1,
wherein the second focusing part includes fourth, fifth and sixth orifice lenses of which inner diameters are df4, df5 and df6, respectively, and
wherein the inner diameters satisfy the following relation:

df4<df5<df6.

5. An aerodynamic lens, comprising:
a cylindrical hollow body having an inlet and an outlet;
a plurality of lenses formed in the body; and
a convergence-divergence nozzle formed at an outlet of the body, wherein the convergence-divergence nozzle includes:
  a nozzle hole formed at a center thereof to allow the passage of particle; and
  a convergence slant surface and a divergence slant surface formed at front and rear portions thereof to form a convergence angle ($\delta$) and a divergence angle ($\theta$) with respect to a central axis of the nozzle hole, respectively.

6. The aerodynamic lens according to claim 5,
wherein the convergence angle ($\delta$) of the convergence-divergence nozzle is set greater than the divergence angle ($\theta$).

* * * * *